(12) United States Patent
Smith et al.

(10) Patent No.: US 6,417,156 B1
(45) Date of Patent: Jul. 9, 2002

(54) ANTI-STATIC ARTICLE

(75) Inventors: Mickey Lee Smith, Winston-Salem; Cynthia Stewart Stokes, Lexington; Ronnie Lee Willard, Clemmons, all of NC (US)

(73) Assignee: R. J. Reynolds Tobacco Company, Winston-Salem, NC (US)

( * ) Notice: Subject to any disclaimer, the term of this patent is extended or adjusted under 35 U.S.C. 154(b) by 0 days.

(21) Appl. No.: 08/827,656

(22) Filed: Apr. 9, 1997

(51) Int. Cl.[7] .................................................. C11D 3/50
(52) U.S. Cl. ......................... 510/515; 510/519; 510/520
(58) Field of Search ................................ 131/270, 273, 131/335, 362, 363, 364, 365; 428/905; 252/500, 91, 174.13, 174.14; 510/515, 519, 520

(56) References Cited

U.S. PATENT DOCUMENTS

| | | | |
|---|---|---|---|
| 2,342,853 A | | 2/1944 | Furstenberg |
| 2,979,268 A | | 4/1961 | Brun |
| 3,347,231 A | | 10/1967 | Chang |
| 3,631,856 A | * | 1/1972 | Taylor ......................... 131/170 |
| 3,683,936 A | | 8/1972 | O'Neil, Jr. |
| 3,685,521 A | * | 8/1972 | Dock ........................... 131/187 |
| 4,345,716 A | * | 8/1982 | Armstrong et al. ............ 239/56 |
| 4,420,002 A | * | 12/1983 | Cline ........................... 131/334 |
| 4,854,332 A | * | 8/1989 | Hanakura .................... 131/365 |
| 4,862,905 A | * | 9/1989 | Green, Jr. et al. .......... 131/84.1 |
| 4,941,483 A | | 7/1990 | Ridings et al. |
| 4,995,407 A | | 2/1991 | Kossiakoff et al. |
| 5,069,231 A | | 12/1991 | Rutherford |
| 5,070,891 A | | 12/1991 | Rutherford |
| 5,145,595 A | * | 9/1992 | Morris et al. .................. 252/91 |
| 5,173,200 A | * | 12/1992 | Kellett ......................... 252/8.8 |
| 5,196,171 A | | 3/1993 | Peltier |
| 5,387,285 A | * | 2/1995 | Rivers ......................... 118/325 |
| 5,588,446 A | * | 12/1996 | Clearman .................... 131/194 |

FOREIGN PATENT DOCUMENTS

| | | |
|---|---|---|
| EP | 0 295 518 A1 | 12/1988 |
| EP | 0 713 655 A3 | 5/1996 |
| EP | 0 713 655 A2 | 5/1996 |
| FR | 1 006 148 | 1/1952 |
| GB | 2 110 524 A | 6/1983 |
| WO | WO 88/03765 | 6/1988 |

* cited by examiner

Primary Examiner—Sean Vincent

(57) ABSTRACT

An odorizer or freshener article for use in odorizing and freshening drawers, closets, cabinets, rooms and the like comprises a rod made of a gathered web or filamentary tow material in which a fragrance is embedded or injected in liquid or powder form or in a breakable fragrance-containing capsule and about which a sheet material is overwrapped. An anti-static additive may be incorporated into the rod for use in a clothes dryer. The components of the article are especially designed to be fabricated using conventional cigarette filter making and cigarette packaging machinery.

7 Claims, 1 Drawing Sheet

ANTI-STATIC ARTICLE

FIELD OF THE INVENTION

The present invention relates to an odorizer, freshener, or deodorizer article and a method of making the same and more particularly to a rod-shaped odorizer device provided with a fragrance or aromatic material that is organoleptically sensed by the user and to a method of making the device from a continuous rod in a process similar to making a cigarette filter rod.

BACKGROUND OF THE INVENTION

It is well known to provide odorizers, air fresheners and sachet-type devices for use in clothes closets, drawers, cabinets and rooms for freshening the air in such spaces and for providing an organoleptically pleasing scent, aroma, or the like. It is also known to place aromatic substances in drawers and closets for use as insect repellents, e.g., moth repellents and the like.

In the cigarette filter making art it is known to inject a liquid flavorant or to deposit a flavor-emitting pellet in the filter tow as the filter is being formed. Apparatus for making such flavor-containing filters are disclosed, for example, in U.S. Pat. No. 4,862,905 and U.S. patent application Ser. No. 07/892,082, both assigned to the assignee of the present invention.

It would be desirable to employ known conventional apparatus and methods for mass producing cigarette components such as cigarette filters in the mass production of odorizers, deodorizers or air freshener articles. Moreover, it would be desirable to provide odorizer or air freshener articles which can be easily, conveniently and inexpensively packaged in a manner similar to packaging cigarettes.

SUMMARY OF THE INVENTION

The present invention is directed to an odorizer or freshener article or device and a method of making the same. The odorizer or freshener article has a design and construction suitable for manufacture on conventional cigarette making and/or cigarette filter making machinery. The odorizer or freshener article comprises a cigarette filter-type rod substrate made of a fibrous tow or a gathered web, overwrapped with a paper, plastic or foil overwrap and cut to any appropriate length, preferably a length suitable for packaging the product in conventional cigarette packaging machinery. An odorizer, deodorizer, fragrance, aromatic material or other organoleptically pleasing substance is embedded in the fibrous tow or web either by liquid or powder injection or by other equivalent means such as insertion into the tow or web of a breakable capsule made of wax or gelatin. The overwrap may be a substantially porous material, such as paper, so as to permit release of the fragrance from all surfaces of the rod-shaped device. The overwrap may also include a fragrance or odorizer. The fibrous or gathered web and/or overwrap material may be dyed or colored in some way to reflect the fragrance or odorizer used. For example: yellow for lemon. On the other hand, if a slower release of the fragrance is desired, the overwrap may be a substantially impervious sheet material, such as a polymeric film, a paper/foil laminate, a paper/foil/paper laminate or a metal foil, so that the fragrance is released only from the tow or web and only at the ends of the device. The polymeric film may also have a metal foil laminated thereto or have a metal layer deposited thereon as by vapor deposition or the like. The fragrance release rate may be further controlled by perforation of any of the foregoing overwraps. The overwrap may be a textured sheet material or may be printed with an ornamental design or other indicia directly on the paper, foil or on the deposited metal surface. A second wrap may be used with an ornamental design for visual enhancement of the device.

The fragrance, odorizer or aromatic material may be selected from any number of known artificial and natural materials or oils, such as, for example, peppermint, spearmint, wintergreen, menthol, cinnamon, vanillin, potpourri and the like. The material may be a moth repellent, such as naphthalene, or any other fragrance-emitting or aromatic material.

In one embodiment of the invention, a gathered web of a polymeric material, such as a polypropylene web, or a filamentary tow material, such as a cellulose acetate, polyester, polypropylene or rayon tow, is formed into a continuous rod on a conventional filter making machine and a fragrance in a liquid or powder form is injected continuously or intermittently into the web or tow at the garniture or bustle of the filter making apparatus prior to overwrapping the rod. The rod is then overwrapped with a porous or impervious sheet material and is then cut into individual rods of appropriate length which may be packaged like cigarettes in conventional cigarette packaging machinery.

In another embodiment of the invention, a breakable wax or gelatin capsule containing a liquid fragrance may be embedded in the rod material of each odorizer or freshener article. When fragrance delivery is desired, the consumer simply squeezes the device at the location of the capsule to break it and release the fragrance into the surrounding rod material.

In a further embodiment of the invention, the filamentary tow, gathered web or the overwrap sheet material may include an anti-static additive as well as a fragrance for use in a clothes dryer to impart a fresh scent to clothing being dried and to minimize static electricity in the clothing resulting from the drying process.

Advantageously, the present invention makes it possible to modify and use conventional cigarette making and cigarette filter making processes and apparatus to mass produce at low cost an odorizer or freshener article.

With the foregoing and other objectives, features and advantages of the invention that will become hereinafter apparent, the invention may be more clearly understood by reference to the following detailed description of the invention , the appended claims and the several views illustrated in the drawings attached hereto.

DETAILED DESCRIPTION OF THE INVENTION

Figure 1:
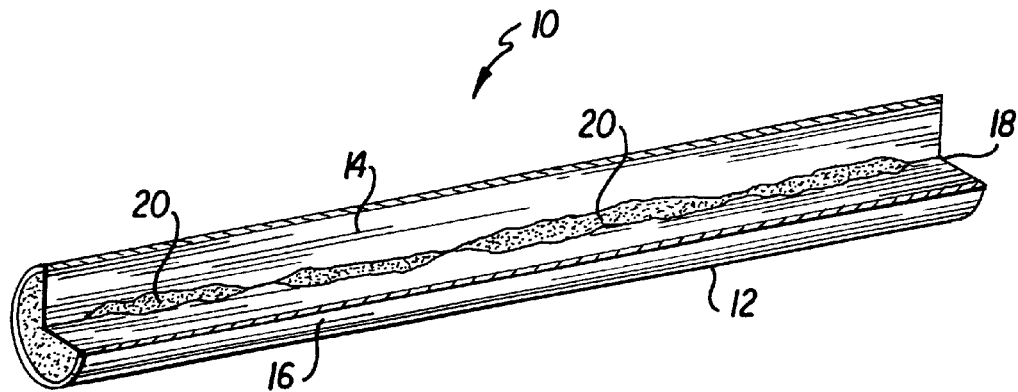
FIG. 1 is a partly sectioned perspective view of one embodiment of the odorizer or freshener article of the present invention.

Referring first to FIG. 1, there is shown in perspective a partially sectioned odorizer or freshener article or device 10 made according to the present invention. Device 10 comprises an elongated cylindrical rod 12 made of a gathered web or filamentary tow substrate 14, such as a gathered paper or polymeric (polypropylene) web, a cellulose acetate, polypropylene, rayon or polyester tow, according to conventional cigarette filter making processes. The rod 12 is circumscribed with an overwrap paper 16 which may be a conventional cigarette wrapping paper, such as 646 grade paper, or a polymeric film with or without a deposited metal layer, a paper/foil or paper/foil/paper laminate, a foil or other suitable sheet material. The paper 16 may be textured or printed with a design and perforated to control the release of the fragrance. Although it should be understood that the dimensions of the rod 12 may vary substantially, one example of a suitably dimensioned device 10 that is readily packaged using conventional cigarette packaging machinery has a rod length of about 80 mm with a circumference of about 25 mm. The length of the odorizer or freshener article or device 10 is preferably about 40 mm or greater with a preferred length range of from about 40 mm up to about 250 mm with a circumference range of about 15 mm to about 40 mm.

Disposed in the rod substrate 14, preferably, but not necessarily along the longitudinal axis 18 of the rod 12, is a fragrance or aromatic material 20, preferably in the form of a liquid or powder which has been injected along the axis 18 of the rod during formation of a continuous rod from which the rod 12 is cut. The continuous rod is preferably formed in the garniture of a conventional cigarette filter making machine. In the embodiment of FIG. 1, the material 20 may be injected along the axis 18 in intermittent cycles timed with the rod cut-off mechanism of the filter making apparatus. In this way, the fragrance material 20 may be spaced from each end of the rod 12 a distance d in the range of 5 mm to 25 mm so that it does not come in direct contact with clothing, etc. that may be in the drawer or space where the odorizer or freshener article 10 is placed.

It is, of course, possible to inject the material 20 into the rod continuously so that the material 20 extends from end to end of the rod 12. It will be appreciated by those skilled in the art that by appropriate timing of the fragrance injection and cutting cycles of the filter rod making apparatus, the fragrance material may be positioned at any one or more axial location or locations along the axis 18 of rod 12 and may have any desired length or lengths along such axis. An anti-static additive may also be injected into the rod substrate or may be otherwise incorporated by conventional processes in the overwrap. In that way, the odorizer or freshener article 10 may be used in a clothes dryer to impart a fresh scent to clothing dried in the dryer and to inhibit static electricity that causes the items of clothing to cling to one another.

In one preferred form, the rod substrate 14 is made of a gathered polypropylene web. Many fragrances are less absorbed by polypropylene than by cellulose acetate and therefore transfer the fragrance more efficiently to the surrounding environment than does cellulose acetate. Polyester filamentary tow is another material that may be advantageously used as the rod substrate 14. The fragrance is also not well absorbed by the polyester material and, like the polypropylene web, transfers the fragrance more efficiently to the surrounding environment. Cellulose acetate tow may also be used as the rod substrate 14. Although it has some disadvantages as described above, it has the advantages that it is less expensive and easier to handle than the polypropylene web or other tow materials.

To use the odorizer or freshener article 10 of FIG. 1, no activation of the fragrance is necessary. The article 10 is simply removed from its conventional package and placed in a desired location, e.g., a drawer, closet, cabinet, shelf, room, etc. As the fragrance or aromatic material 20 dissipates into the surrounding air, it is organoleptically sensed in the usual manner when the drawer, closet or cabinet is opened.

Figure 2:
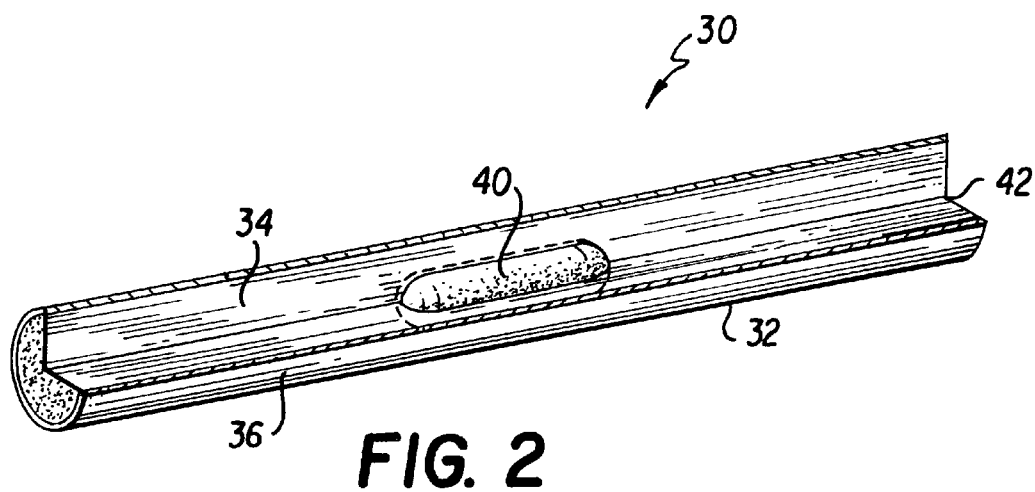
FIG. 2 is a partly sectioned perspective view of another embodiment of the odorizer or freshener article of the present invention.

Referring now to FIG. 2, there is shown a second embodiment of the odorizer or freshener article 10 of the invention which is designated generally by reference numeral 30. Article 30 is the same in all respects as article 10 of FIG. 1 with the exception of the fragrance material. Device 30 comprises a rod 32 made of a gathered web or filamentary tow substrate 34 circumscribed by a paper, plastic or foil overwrap 36. Instead of injecting a fragrance in a liquid or powder form into the substrate, capsules 40 containing a liquid fragrance are inserted into the continuous rod substrate 34 at spaced intervals such that when the rod 32 is cut into individual articles 30, one or more capsules is embedded along the axis 42 of the rod 32. It will be appreciated that a plurality of fragrance-containing microcapsules may also be inserted into the rod substrate.

Capsule 40 is preferably made of a breakable biodegradable material, such as gelatin, but may be made of other breakable materials such as wax or the like. The volume of the capsule 40 may vary depending on the quantity of liquid fragrance necessary to achieve the desired organoleptic effect. Storage of the fragrance in the capsule 40 substantially increases the shelf life of the odorizer or freshener article. To use the device 30 of FIG. 2, the rod 32 is grasped and squeezed between the fingers at the location of the capsule 40 until the capsule ruptures or breaks and releases the fragrance into the rod substrate. Thereafter, the device is used in the same way as the device 10.

Advantageously, the less expensive cellulose acetate tow is the preferred rod substrate 34 in the FIG. 2 embodiment since the device is used substantially concurrently with release of the fragrance. Typically, loss of fragrance by volatilization or by absorption into the substrate occurs over an extended period of time and is therefore of no concern in the FIG. 2 embodiment.

It will be appreciated that the present invention provides an efficient and economical way of mass producing an odorizer or freshener article or sachet-type device using existing cigarette filter making and packaging machinery. The several embodiments of the article are novel combinations of components and materials especially suited to provide effective transfer of the fragrance to the surrounding atmosphere so as to achieve the desired organoleptic effect.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. An article for use as an anti-static device in a clothes driver to inhibit static electricity that causes the items of clothing to cling to one another, comprising a rod formed with the shape and appearance of an elongated cigarette filter having a longitudinal axis, two ends and being made of a gathered web or filamentary tow substrate extending from end to end of said rod, said rod being overwrapped with a sheet material overwrap, and an anti-static additive incorporated in said rod.

2. The article of claim 1, wherein said sheet material overwrap is a porous paper.

3. The article of claim 1, wherein said sheet material overwrap is perforated.

4. The article of claim 1, wherein said anti-static additive is incorporated in the web or tow substrate.

5. The article of claim 1, wherein said anti-static additive is incorporated in the sheet material overwrap.

6. The article of claim 1, including a fragrance incorporated in said rod to impart a fresh scent to the clothing.

7. The article of claim 1, wherein said rod substrate is made of a polypropylene, polyester or cellulose acetate tow, said anti-static additive being in the form of a liquid or powder injected along the axis of said rod.

* * * * *

UNITED STATES PATENT AND TRADEMARK OFFICE
CERTIFICATE OF CORRECTION

PATENT NO.   : 6,417,156 B1
DATED        : July 9, 2002
INVENTOR(S)  : Smith et al.

It is certified that error appears in the above-identified patent and that said Letters Patent is hereby corrected as shown below:

<u>Title page,</u>
Item [*] Notice, delete "0" and insert -- 669 --.

Signed and Sealed this

Sixteenth Day of August, 2005

JON W. DUDAS
*Director of the United States Patent and Trademark Office*